(12) United States Patent
Wagner et al.

(10) Patent No.: US 8,986,662 B2
(45) Date of Patent: Mar. 24, 2015

(54) USE OF SILANE AND SILOXANE BIS(BIPHENYL) TRIAZINE DERIVATIVES AS UV ABSORBERS

(75) Inventors: Barbara Wagner, Lorrach (DE); Bernd Herzog, Grenzach-Wyhlen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/878,763

(22) PCT Filed: Oct. 20, 2011

(86) PCT No.: PCT/EP2011/068303
§ 371 (c)(1),
(2), (4) Date: Apr. 11, 2013

(87) PCT Pub. No.: WO2012/052499
PCT Pub. Date: Apr. 26, 2012

(65) Prior Publication Data
US 2013/0202542 A1    Aug. 8, 2013

Related U.S. Application Data

(60) Provisional application No. 61/405,651, filed on Oct. 22, 2010.

(30) Foreign Application Priority Data

Oct. 22, 2010  (EP) ..................................... 10188474

(51) Int. Cl.
- *A61K 8/00* (2006.01)
- *A61K 8/49* (2006.01)
- *A61K 8/58* (2006.01)
- *A61K 8/898* (2006.01)
- *A61Q 17/04* (2006.01)
- *C07F 7/08* (2006.01)

(52) U.S. Cl.
CPC ................ *A61K 8/585* (2013.01); *A61K 8/898* (2013.01); *A61Q 17/04* (2013.01); *C07F 7/0854* (2013.01)
USPC ............................................ 424/59; 424/70.9

(58) Field of Classification Search
USPC ................................................... 424/59, 70.9
See application file for complete search history.

(56) References Cited

U.S. PATENT DOCUMENTS 5,976,512 A * 11/1999 Huber .............................. 424/59
8,715,406 B2 * 5/2014 Meyer Zu Bernstenhorst et al. ......... 106/287.11
2003/0045444 A1 3/2003 Fletcher et al.

FOREIGN PATENT DOCUMENTS

| EP | 0863145 A2 | 9/1998 |
| EP | 0933376 A2 | 8/1999 |
| WO | 2010127805 A1 | 11/2010 |

OTHER PUBLICATIONS

EP Search Report dated Mar. 11, 2011.
International Search Report dated Apr. 23, 2014.
English language abstract of EP 0863145 Sep. 9, 1998.

* cited by examiner

*Primary Examiner* — Blessing M Fubara
*Assistant Examiner* — Jennifer A Berrios
(74) *Attorney, Agent, or Firm* — Sheila A. Loggins

(57) ABSTRACT

Disclosed is the use of silane and siloxane bis(biphenyl) triazine derivatives of formula (1), wherein n is a number from 1 to 4; if n=1, X is *-L-Sil; or a radical of formula (11'), L is a linker selected from a radical of formula (2); R1, R2, R3 independently from each other are $C_1$-$C_{22}$alkyl; $C_6$-$C_{20}$aryl; $C_1$-$C_{22}$alkoxy; or O—$C_6$-$C_{20}$aryl; R4, R5, R6 and R7 independently from each other are hydrogen; $C_1$-$C_{22}$alkyl; $C_6$-$C_{20}$aryl; $C_1$-$C_{22}$alkoxy; or O—$C_6$-$C_{20}$aryl; b is a number from 0 to 30; c is a number from 0 to 6; and d is a number from 0 to 1; p is a number from 1 to 250; q is a number from 0 to 250; and Sil, $Sil_1$ and $Sil_2$ independently from each other are a silane-, oligosiloxane or polysiloxane moiety; if n=2, X is a bivalent radical of formula (1a); or (1b); x is a number from 2 to 250; y is a number from 0 to 250; and z is a number from 1 to 50; if n=3, X is a trivalent radical containing a silane-, oligosiloxane or polysiloxane moiety; If n=4, X is a tetravalent radical of formula (1c); and A is a radical of formula (111') as UV absorbers.

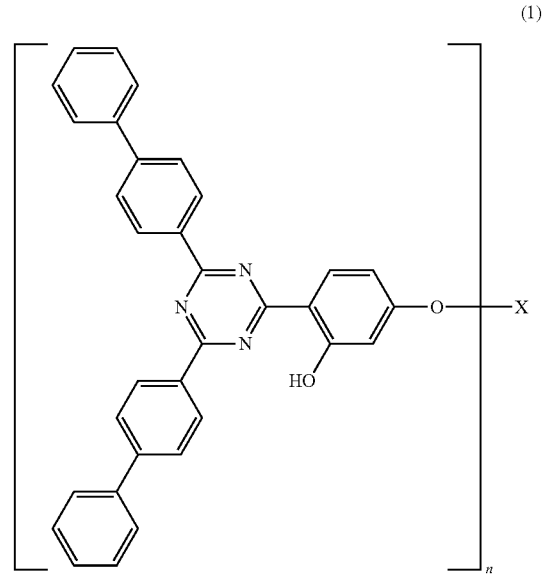

(1)

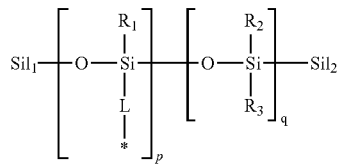
(11')
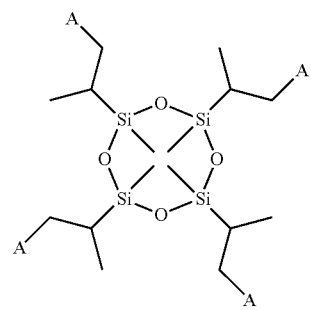
(1c)
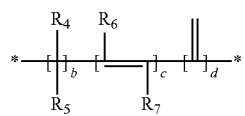
(2)
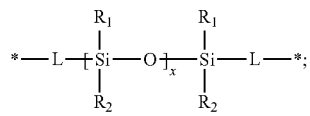
(1a)
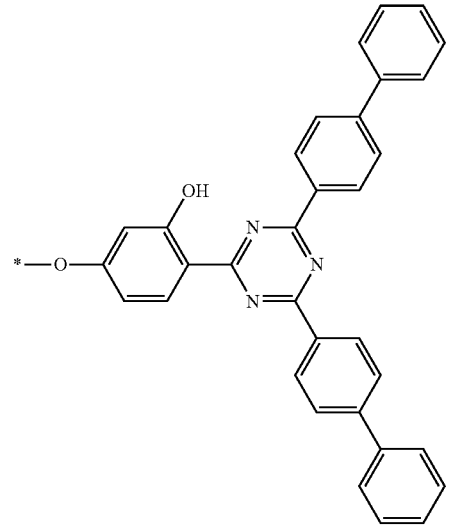
(111')
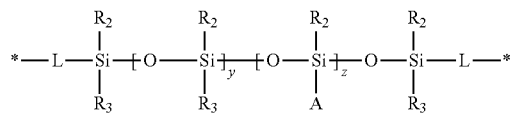
(1b)
13 Claims, No Drawings

USE OF SILANE AND SILOXANE BIS(BIPHENYL) TRIAZINE DERIVATIVES AS UV ABSORBERS

The present invention relates to the use of novel silane, siloxane or polysiloxane bisbiphenyl-triazine derivatives as UV absorbers and their use in sunscreens and/or cosmetic compositions.

It is well known that ultraviolet radiation (light) is harmful to human skin. Depending on the wavelength UV radiation causes different types of skin damage. UV-B radiation (about 290 to about 320 nm) is responsible for sunburn and can cause skin cancer. UV-A radiation (about 320 to about 400 nm) while producing tanning of the skin, contributes also to sunburn and the induction of skin cancers. Moreover, the harmful effects of the UV-B radiation may be aggravated by UV-A radiation.

Therefore, an effective sunscreen formulation preferably comprises both at least one UV-A and UV-B filter and a broad band UV filter covering the full range from about 290 nm to about 400 nm to prevent the human skin from the damage of sunlight.

Besides their screening power on solar radiation UV filters must also have good resistance to water and perspiration and also satisfactory photostability.

Unfortunately, many effective organic UV filters have a poor oil-solubility at a certain concentration and tend to crystallization. As a consequence the UV protection efficacy is significantly decreased.

It is known that there are lipophilic UV filters like Butyl Methoxydibenzoylmethane (sold under the tradename "Parsol 1789" by DSM) which have the particularity and also the disadvantage of being solid at ambient temperature. As a result, their use in sunscreen cosmetic compositions implies certain constraints in terms of their formulation and their use, in particular the selection of specific suitable cosmetic solvents that afford a proper solubility of these UV filters. Thus, a UV filter should show high solubility in common cosmetic oils or should be a good solvent for other UV filters that show poor oil solubility.

Moreover the oil soluble UV filters should be included in cosmetic sun care products without any impact on the sensorial characteristic of the emulsion. For that reason the optimal distribution of the UV absorber within the hydro-lipid film left on the skin after spreading should be guaranteed.

It is therefore an object of the present invention to find UV absorber formulations which have improved properties regarding the UV absorber.

Surprisingly it has been found that specific silane and siloxane bis(biphenyl)triazine derivatives have very good properties as cosmetic UV-B absorbers.

Therefore, the instant invention relates to the use of silane and siloxane bis(biphenyl)triazine derivatives as UV absorbers represented by the following general formula

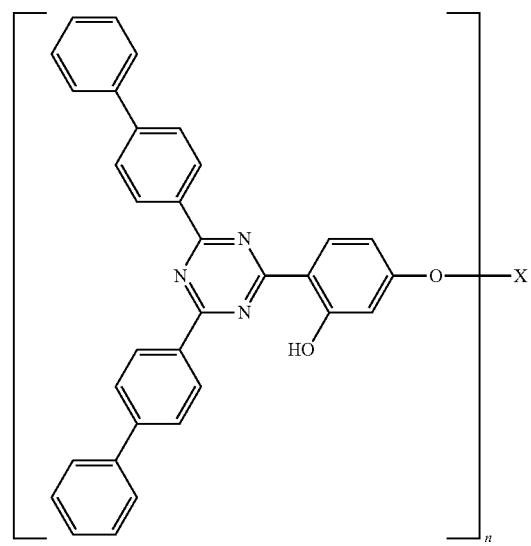

(1)

wherein
n is a number from 1 to 4;
if n=1,
X is *-L-Sil; or a radical of formula

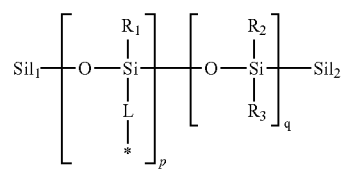

L is a linker selected from a radical of formula

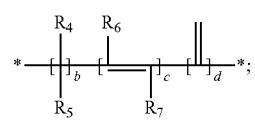

(2)

$R_1$, $R_2$, $R_3$ independently form each other are $C_1$-$C_{22}$alkyl; $C_6$-$C_{20}$aryl; $C_1$-$C_{22}$alkoxy; or O—$C_6$-$C_{20}$aryl;

$R_4$, $R_5$, $R_6$ and $R_7$ independently from each other are hydrogen; $C_1$-$C_{22}$alkyl; $C_6$-$C_{20}$aryl; $C_1$-$C_{22}$alkoxy; or O—$C_6$-$C_{20}$aryl;

b is a number from 0 to 30;
c is a number from 0 to 6; and
d is a number from 0 to 1;
p is a number from 1 to 250;
q is a number from 0 to 250; and
Sil, $Sil_1$ and $Sil_2$ independently from each other are a silane-, oligosiloxane or polysiloxane moiety;

if n=2,
X is a bivalent radical of formula

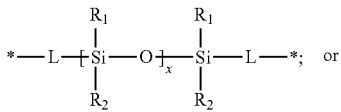 (1a)

or

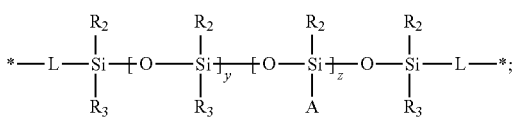 (1b)

x is a number from 2 to 250;
y is a number from 0 to 250; and
z is a number from 1 to 50;
if n=3,
X is a trivalent radical containing a silane-, oligosiloxane or polysiloxane moiety;
If n=4,
X is a tetravalent radical of formula

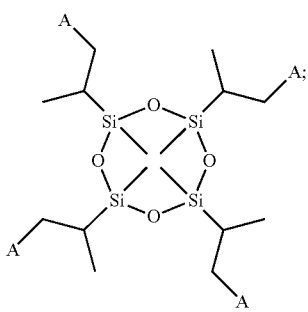 (1c)

and
A is a radical of formula

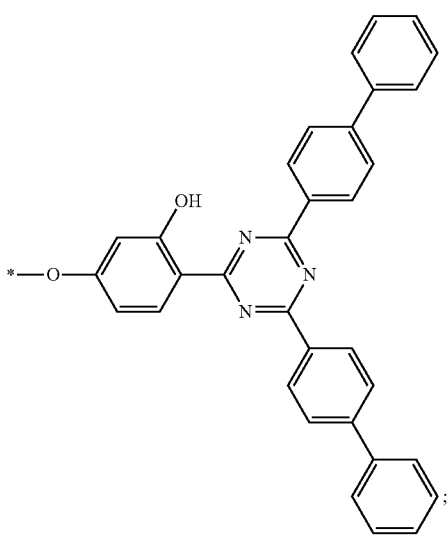

as UV absorbers.

Preferred are compounds of formula (1), wherein
n is a number from 1 to 4;
if n=1,
X is *-L-Sil;
L is a linker selected from a radical of formula

 (2)

$R_4$, $R_5$, $R_6$ and $R_7$ independently from each other are hydrogen; $C_1$-$C_{22}$alkyl; $C_6$-$C_{20}$aryl; $C_1$-$C_{22}$alkoxy; or O—$C_6$-$C_{20}$aryl;
b is a number from 0 to 30;
c is a number from 0 to 6; and
d is a number from 0 to 1;
Sil, $Sil_1$ and $Sil_2$ independently from each other are a silane-, oligosiloxane or polysiloxane moiety;
$R_1$, $R_2$, $R_3$ independently form each other are $C_1$-$C_{22}$alkyl; $C_6$-$C_{20}$aryl; $C_1$-$C_{22}$alkoxy; or O—$C_6$-$C_{20}$aryl;
x is a number from 2 to 250;
y is a number from 0 to 250; and
z is a number from 1 to 50;
if n=3,
X is a trivalent radical containing a silane-, oligosiloxane or polysiloxane moiety;
If n=4,
X is a tetravalent radical of formula (1c).
Preferably Sil is an oligosiloxane moiety selected from $Si(R_1)_m[OSi(R_2)]_o$; wherein
m is 0; 1; or 2,
o is 3, 2 or 1;
the sum of m and o are 3; and
$R_1$ and $R_2$ independently form each other are $C_1$-$C_{22}$alkyl; $C_6$-$C_{20}$aryl; $C_1$-$C_{22}$alkoxy; or O—$C_6$-$C_{20}$aryl.
Preferred silane groups are trimethylsilane, triethylsilane, tripropylsilane, triisopropylsilane, dimethyl tert-butylsilane, dimethylhexylsilane, triphenylsilane, dimethylphenylsilane and the like.
Further preference is given to the use of a mixture of the herein described bisbiphenyl triazines.
Preference is given to compounds of formula (2), wherein
$R_4$ and $R_5$, independently from each other are hydrogen; or $C_1$-$C_{22}$alkyl,
b is a number from 1 to 30; and
c and d are 0.
Even more preferred are compounds of formula (2), wherein
$R_4$ and $R_5$, independently from each other are hydrogen; or $C_1$-$C_5$alkyl; or compounds of formula (2), wherein $R_4$ and $R_5$, independently from each other are hydrogen; or methyl.
Most preferred are compounds of formula (2) wherein
b is a number from 1 to 5.
Most preferred are compounds of formula (1) wherein X corresponds to the formula

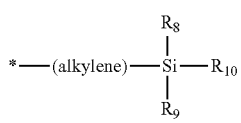
(3)

Wherein
"alkylene" denotes a straight chained or branched $C_2$-$C_{12}$alkylene;
$R_8$, $R_9$ and $R_{10}$ independently from each other are $C_1$-$C_{22}$alkyl; or $C_1$-$C_{22}$alkoxy; or a radical of formula

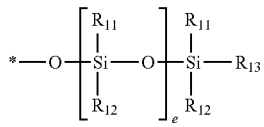
(3a)

$R_{11}$ and $R_{12}$ and $R_{13}$ independently form each other are $C_1$-$C_{22}$alkyl; or $C_1$-$C_{22}$alkoxy; and
e is a number from 0 to 30.

Preferred are also compounds of formula (1), wherein X is a radical of formula

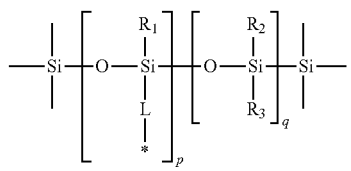

wherein
p and q independently from each other are a number from 1 to 20; and most preferably from 3 to 15.

Examples of bisbiphenyltriazine compounds according to the present invention are listed in Table 1 below:

TABLE 1

Representatives of bisbiphenyltriazines according to the present invention

B-1
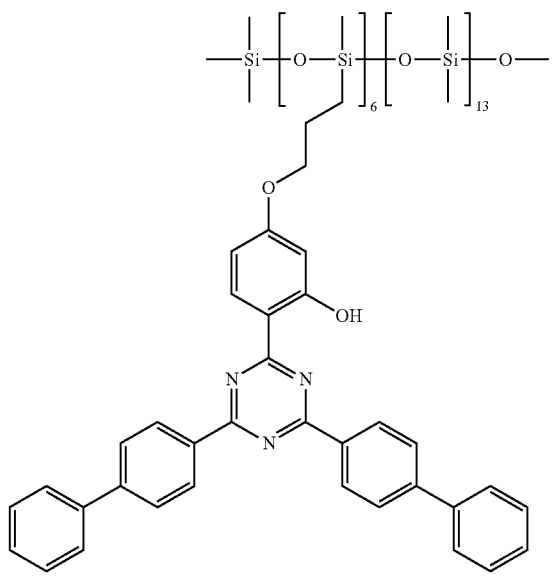

TABLE 1-continued
Representatives of bisbiphenyltriazines according to the present invention
B-2
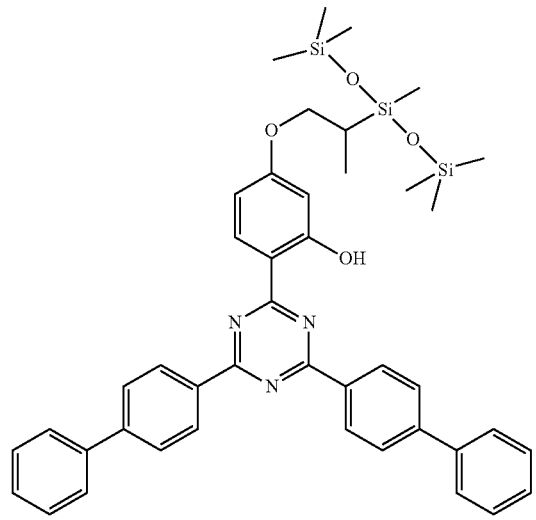 [SMILES: CC(COc1ccc(-c2nc(-c3ccc(-c4ccccc4)cc3)nc(-c3ccc(-c4ccccc4)cc3)n2)c(O)c1)[Si](C)(O[Si](C)(C)C)O[Si](C)(C)C]
B-3
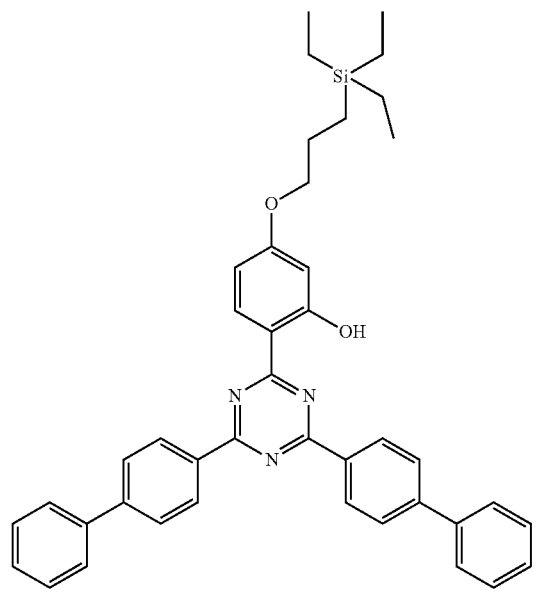 [SMILES: CC[Si](CC)(CC)CCCOc1ccc(-c2nc(-c3ccc(-c4ccccc4)cc3)nc(-c3ccc(-c4ccccc4)cc3)n2)c(O)c1]

TABLE 1-continued
Representatives of bisbiphenyltriazines according to the present invention
B-4
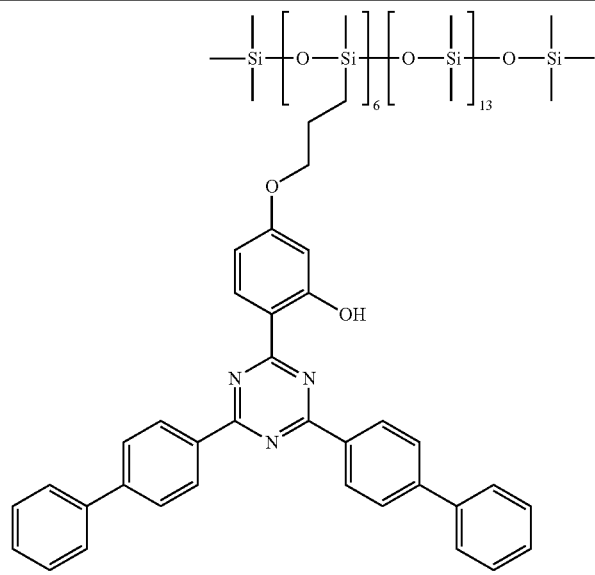
B-5
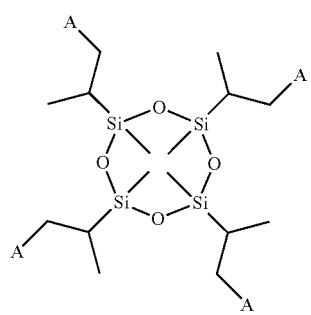
A = 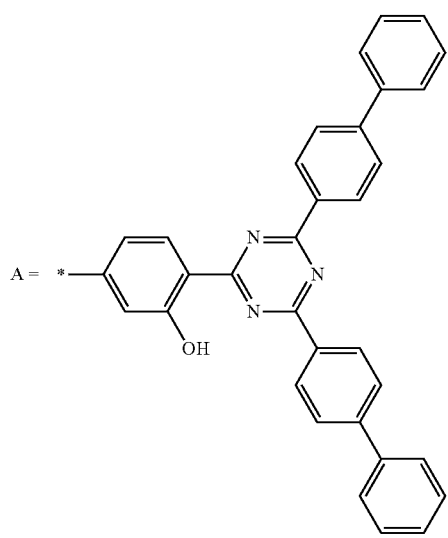

TABLE 1-continued
Representatives of bisbiphenyltriazines according to the present invention
B-6
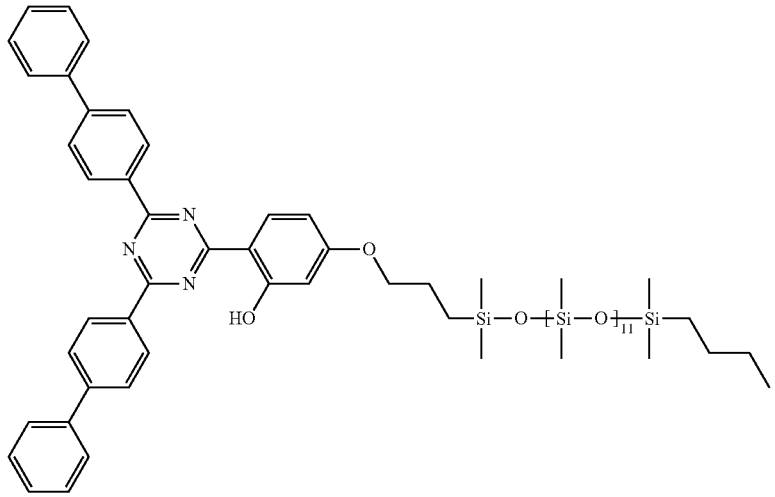
B-7
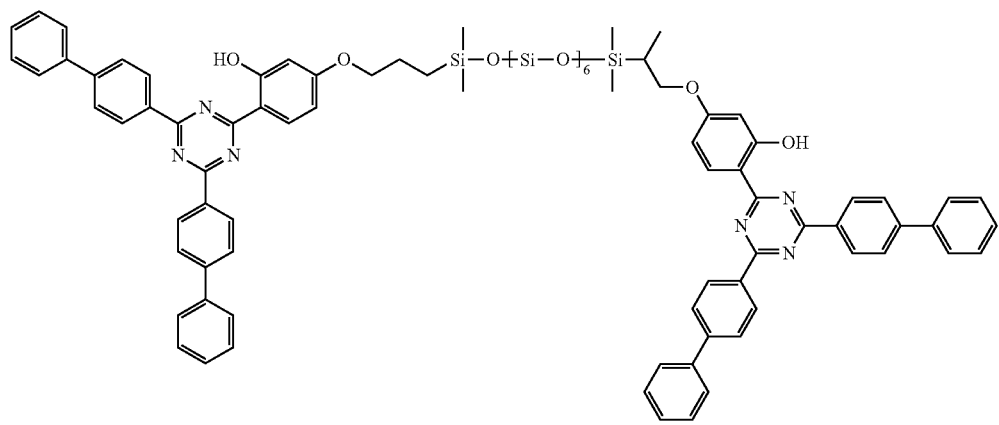
B-8
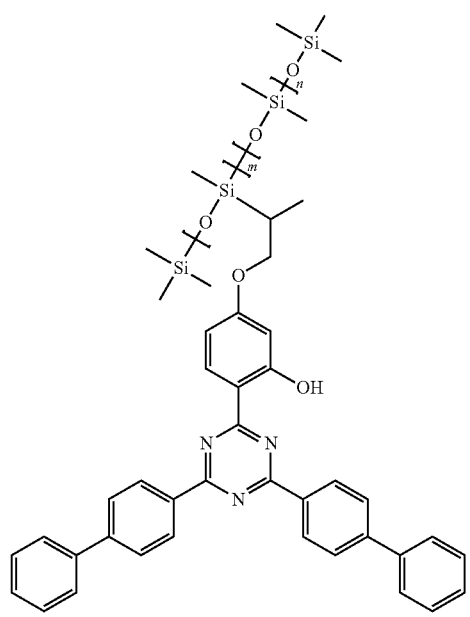
m~10, n~10

TABLE 1-continued
Representatives of bisbiphenyltriazines according to the present invention
B-9
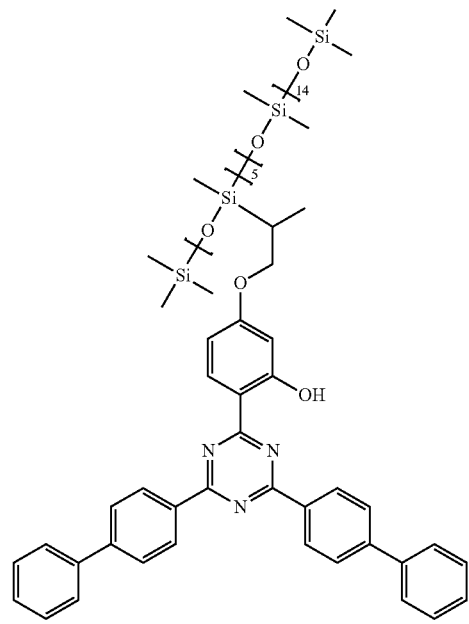
B-10
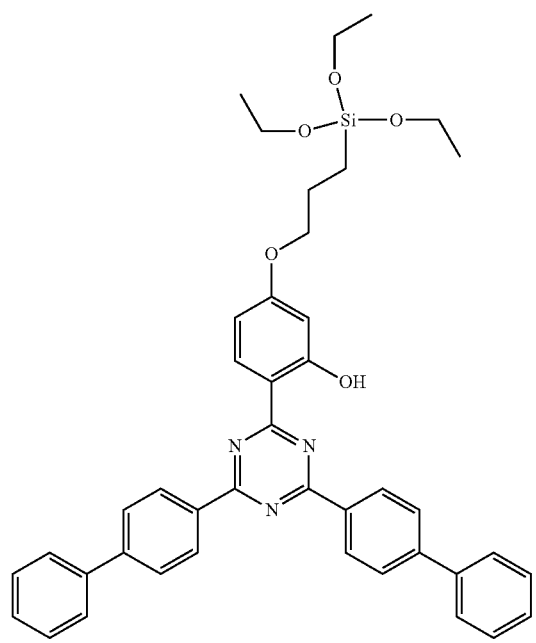 [SMILES: CCO[Si](CCCOc1ccc(-c2nc(-c3ccc(-c4ccccc4)cc3)nc(-c3ccc(-c4ccccc4)cc3)n2)c(O)c1)(OCC)OCC]

The compounds of formula (1) are novel.

Therefore, the present invention also relates to silane and siloxane bis(biphenyl)triazine derivatives of formula

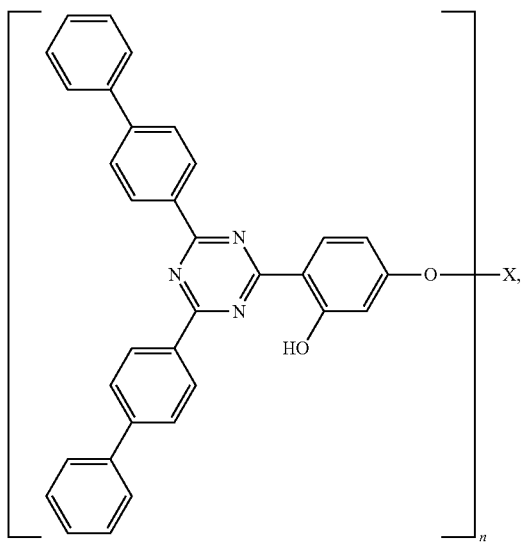
(1)

wherein n is a number from 1 to 4;

if n=1,

X is *-L-Sil; or a radical of formula

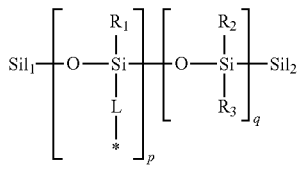

L is a linker selected from a radical of formula

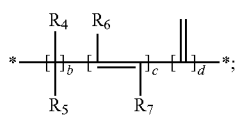
(2)

$R_4$, $R_5$, $R_6$ and $R_7$ independently from each other are hydrogen; $C_1$-$C_{22}$alkyl; $C_6$-$C_{20}$aryl; $C_1$-$C_{22}$alkoxy; or O—$C_6$-$C_{20}$aryl;

b is a number from 0 to 30;

c is a number from 0 to 6; and d is a number from 0 to 1;

p is a number from 1 to 250;

q is a number from 0 to 250; and

Sil, $Sil_1$ and $Sil_2$ independently from each other are a silane-, oligosiloxane or polysiloxane moiety;

if n=2,

X is a bivalent radical of formula

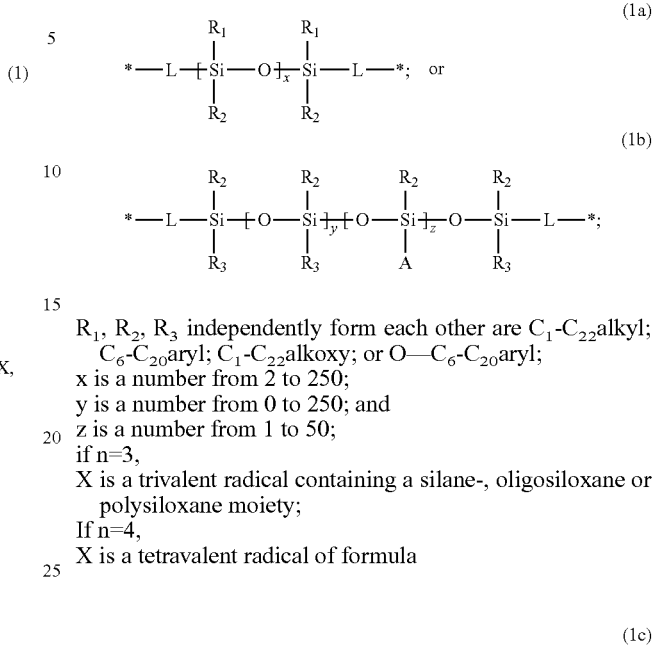

$R_1$, $R_2$, $R_3$ independently form each other are $C_1$-$C_{22}$alkyl; $C_6$-$C_{20}$aryl; $C_1$-$C_{22}$alkoxy; or O—$C_6$-$C_{20}$aryl;

x is a number from 2 to 250;

y is a number from 0 to 250; and z is a number from 1 to 50;

if n=3,

X is a trivalent radical containing a silane-, oligosiloxane or polysiloxane moiety;

If n=4,

X is a tetravalent radical of formula

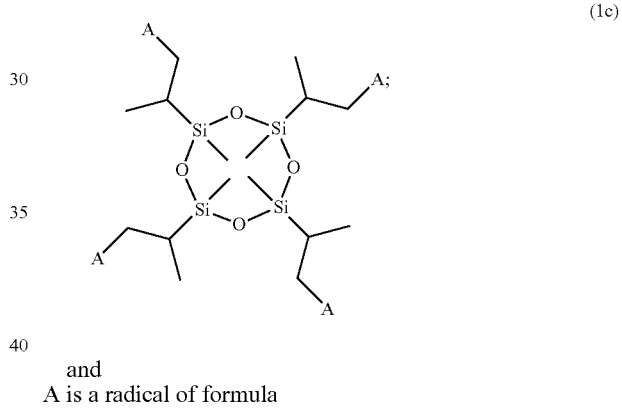
(1c)

and

A is a radical of formula

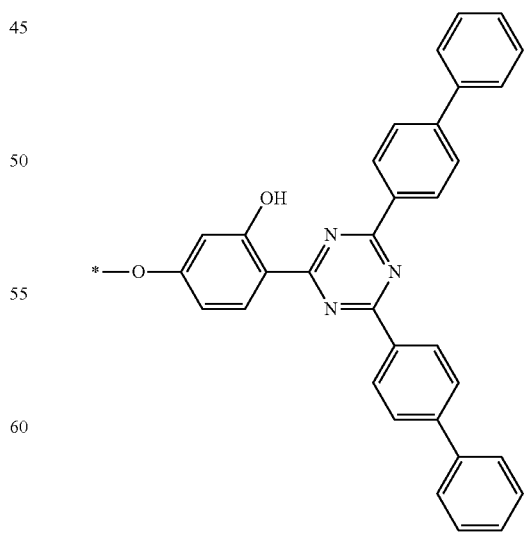

The compounds of formula (1) may be obtained conventionally employing a hydrosilylation reaction starting from compounds of the general formula (1) in which the group X contains an unsaturated C—C bond which can be subsequently hydrosilylated. Such compounds correspond for example to formula (3).

More preferably the group X is an allyl residue.

The hydrosilylation reaction is performed between the unsaturated compound and a SiH containing silane, oligosiloxane and polysiloxane in accordance with the following reaction scheme:

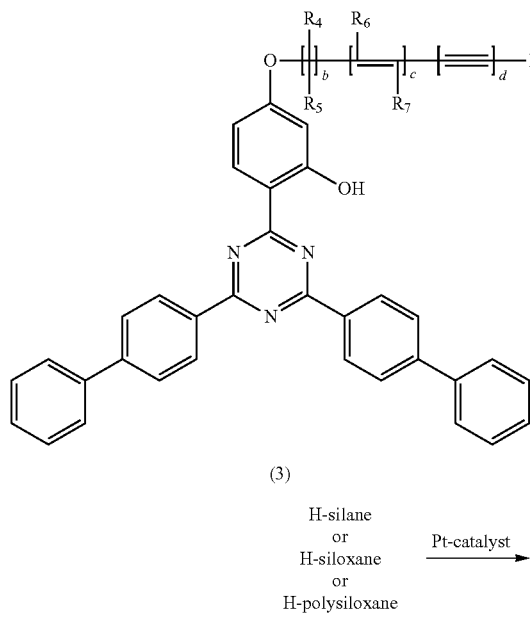

(3)

H-silane
or
H-siloxane    —Pt-catalyst→   (1),
or
H-polysiloxane wherein $R_8$ is hydrogen; $C_1$-$C_{22}$alkyl; $C_6$-$C_{20}$aryl; $C_1$-$C_{22}$alkoxy; or O—$C_6$-$C_{20}$aryl;

b is a number from 0 to 30;

c is a number from 0 to 6; and d is a number from 0 to 1; wherein at least one of c or d is not 0.

The hydrosilylation reaction is performed in the presence of a hydrosilylation catalyst.

Preferably the catalyst is a platinum(0) catalyst, most preferred it is the so-called Karstedt catalyst.

In general a mixture of the corresponding regioisomers of the hydrosilylation adducts is formed.

The following reaction scheme exemplifies the hydrosilylation reactions.

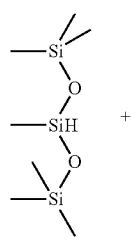

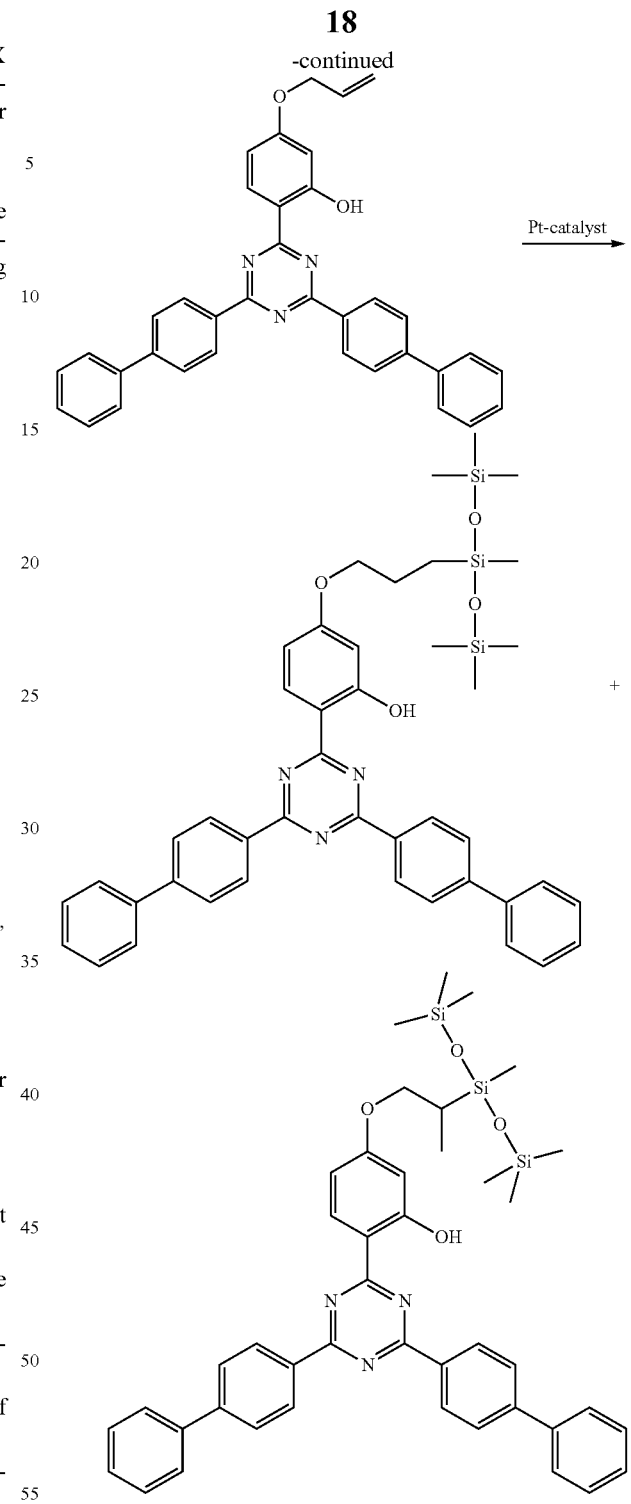

The silane and siloxane bis(biphenyl)triazine derivatives according to formula (1) may advantageously be used as actives in cosmetic preparations which additionally comprise cosmetically tolerable carriers or adjuvants.

The cosmetic preparation may also comprise, in addition to the mixtures of silane and siloxane bis(biphenyl)triazine derivatives according to formula (1) one or more further UV protective agents of the following substance classes:

1. p-aminobenzoic acid derivatives, for example 4-dimethylaminobenzoic acid 2-ethylhexyl ester;

2. salicylic acid derivatives, for example salicylic acid 2-ethylhexyl ester;
3. benzophenone derivatives, for example 2-hydroxy-4-methoxybenzophenone and its 5-sulfonic acid derivative;
4. dibenzoylmethane derivatives, for example 1-(4-tert-butylphenyl)-3-(4-methoxyphenyl)propane-1,3-dione;
5. diphenylacrylates, for example 2-ethylhexyl 2-cyano-3,3-diphenylacrylate, and 3-(benzofuranyl) 2-cyanoacrylate;
6. 3-imidazol-4-ylacrylic acid and esters;
7. benzofuran derivatives, especially 2-(p-aminophenyl)benzofuran derivatives, described in EP-A-582 189, U.S. Pat. No. 5,338,539, U.S. Pat. No. 5,518,713 and EP-A-613 893;
8. polymeric UV absorbers, for example the benzylidene malonate derivatives described in EP-A-709 080;
9. cinnamic acid derivatives, for example the 4-methoxycinnamic acid 2-ethylhexyl ester and isoamyl ester or cinnamic acid derivatives disclosed in U.S. Pat. No. 5,601,811 and WO 97/00851;
10. camphor derivatives, for example 3-(4'-methyl)benzylidene-bornan-2-one, 3-benzylidenebornan-2-one, N-[2 (and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylene-dimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate;
11. hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxphenyl)-1,3,5-triazine; 2,4-bis{[4-(2-ethylhexyloxy)-2-hydroxy]-phenyl}-6-[4-(2-methoxyethyl-carboxyl)-phenylamino]-1,3,5-triazine; 2,4-bis{[4-(tris(trimethylsilyloxy-silylpropyloxy)-2-hydroxy]-phenyl}-6-(4-methoxyphenyl)-1,3,5-triazine; 2,4-bis{[4-(2''-methylpropenyloxy)-2-hydroxy]-phenyl}-6-(4-methoxyphenyl)-1,3,5-triazine; 2,4-bis{[4-(1',1',1',3',5',5',5'-heptamethyltrisilyl-2''-methyl-propyloxy)-2-hydroxy]-phenyl}-6-(4-methoxphenyl)-1,3,5-triazine; 2,4-bis{[4-(3-(2-propyloxy)-2-hydroxy-propyloxy)-2-hydroxy]-phenyl}-6-[4-ethylcarboxy)-phenylamino]-1,3,5-triazine;
12. benzotriazole compounds, for example 2,2'-methylene-bis(6-(2H-benzotriazol-2-yl)-4-(1,1,3,3-tetramethylbutyl)-phenol

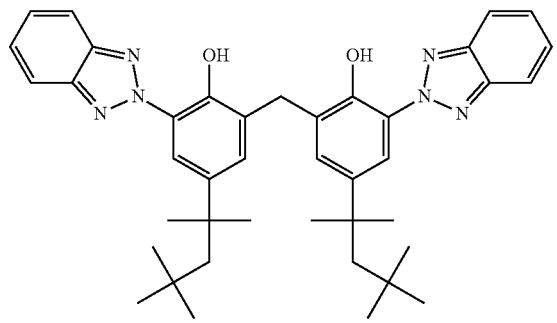

13. trianilino-s-triazine derivatives, for example 2,4,6-trianiline-(p-carbo-2'-ethyl-1'-oxy)-1,3,5-triazine and the UV absorbers disclosed in U.S. Pat. No. 5,332,568, EP-A-517 104, EP-A-507 691, WO 93/17002 and EP-A-570 838;
14. 2-phenylbenzimidazole-5-sulfonic acid and salts thereof;
15. menthyl o-aminobenzoate;
16. $TiO_2$ (variously encapsulated), ZnO and mica.

The UV absorbers described in "Sunscreens", Eds. N. J. Lowe, N. A. Shaath, Marcel Dekker, Inc., New York and Basle or in Cosmetics & Toiletries (107), 50ff (1992) also can be used as additional UV protective substances.

Special preference is given to the light-protective agents indicated in the following Table:

| INCI | Chemical Name | CAS No. |
| --- | --- | --- |
| 3-BENZYLIDENE CAMPHOR | 1,7,7-trimethyl-3-(phenylmethylene)-bicyclo[2.2.1]heptan-2-one | 15087-24-8 |
| 4-METHYLBENZYLIDENE CAMPHOR | (+/−)-1,7,7-trimethyl-3-[(4-methylphenyl)-methylene]bicyclo[2.2.1]heptan-2-one | 36861-47-9 |
| BENZOPHENONE-10 | (2-hydroxy-4-methoxyphenyl)-(4-methyl-phenyl)methanone | 1641-17-4 |
| BENZOPHENONE-1 | 2,4-dihydroxybenzophenone | 131-56-6 |
| BENZOPHENONE-2 | 2,2',4,4'-tetrahydroxybenzophenone | 131-55-5 |
| BENZOPHENONE-3 | 2-hydroxy-4-methoxybenzophenone | 131-57-7 |
| BENZOPHENONE-4 | 2-hydroxy-4-methoxybenzophenone-5-sulfonic acid | 4065-45-6 |
| BENZOPHENONE-6 | 2,2'-dihydroxy-4,4'-dimethoxybenzophenone | 131-54-4 |
| BENZOPHENONE-8 | 2,2'-dihydroxy-4-methoxybenzophenone | 131-53-3 |
| BENZYLIDENE CAMPHOR SULFONIC ACID | alpha-(2-oxoborn-3-ylidene)-toluene-4-sulfonic acid and its salts | 56039-58-8 |
| BUTYL METHOXY-DIBENZOYLMETHANE | 1-[4-(1,1-dimethylethyl)phenyl]-3-(4-methoxyphenyl)propane-1,3-dione | 70356-09-1 |
| CAMPHOR BENZALKONIUM METHOSULFATE | methyl N,N,N-trimethyl-4-[(4,7,7-trimethyl-3-oxobicyclo[2,2,1]hept-2-ylidene)methyl]-anilinium sulfate | 52793-97- |
| CINOXATE | 2-ethoxyethyl p-methoxycinnamate | 104-28-9 |
| DEA-METHOXYCINNAMATE | diethanolamine salt of p-methoxy-hydrocinnamate | 56265-46-4 |
| DIISOPROPYL METHYL CINNAMATE | 2-propenoic acid, 3-[2,4-bis(1-methylethyl)phenyl]-, methyl ester | 32580-71-5 |
| DIPROPYLENE GLYCOL SALICYLATE | dipropylene glycol salicylate | 7491-14-7 |
| ETHYL DIHYDROXYPROPYL PABA | ethyl 4-bis(2-hydroxypropyl)-amino-benzoate | 58882-17-0 |
| ETHYL DIISOPROPYLCINNAMATE | ethyl 3-[2,4-bis(1-methylethyl)phenyl]-acrylate | 32580-72-6 |

| INCI | Chemical Name | CAS No. |
|---|---|---|
| ETHYL METHOXYCINNAMATE | ethyl p-methoxycinnamate | 1929-30-2 |
| GLYCERYL OCTANOATE DIMETHOXYCINNAMATE | | |
| GLYCERYL PABA | glyceryl 1-(4-aminobenzoate) | 136-44-7 |
| HOMOSALATE | 3,3,5-trimethylcyclohexyl-2-hydroxy-benzoate | 118-56-9 |
| ISOAMYL p-METHOXY-CINNAMATE | isopentyl p-methoxycinnamate | 71617-10-2 |
| ISOPROPYL DIBENZOYL-METHANE | 1-[4-(1-methylethyl)phenyl]-3-phenyl-propane-1,3-dione | 63250-25-9 |
| ISOPROPYL METHOXYCINNAMATE | isopropyl p-methoxycinnamate | 5466-76-2 |
| LAWSONE | 2-hydroxy-1,4-naphthoquinone | 83-72-7 |
| MENTHYL ANTHRANILATE | menthyl o-aminobenzoate | 134-09-8 |
| MENTHYL SALICYLATE | menthyl salicylate | 89-46-3 |
| OCTOCRYLENE | 2-ethylhexyl 2-cyano-3,3-diphenyl acrylate | 6197-30-4 |
| ETHYLHEXYL DIMETHYL PABA | 2-ethylhexyl 4-(dimethylamino)benzoate | 21245-02-3 |
| ETHYLHEXYL METHOXY-CINNAMATE | 2-ethylhexyl 4-methoxycinnamate | 5466-77-3 |
| ETHYLHEXYL SALICYLATE | 2-ethylhexyl salicylate | 118-60-5 |
| ETHYLHEXYL TRIAZONE | benzoic acid, 4,4',4''-(1,3,5-triazine-2,4,6-triyltriimino)tris-, tris(2-ethylhexyl) ester; 2,4,6-trianilino-(p-carbo-2'-ethylhexyl-1'-oxy)-1,3,5-triazine | 88122-99-0 |
| PABA | 4-aminobenzoic acid | 150-13-0 |
| PEG-25 PABA | benzoic acid, 4-amino-, ethyl ester, polymer with oxirane | 113010-52-9 |
| PENTYL DIMETHYL PABA | amyl dimethyl PABA | 14779-78-3 |
| PHENYLBENZIMIDAZOLE SULFONIC ACID | 2-phenyl-1H-benzimidazole-5-sulfonic acid | 27503-81-7 |
| POLYACRYLAMIDOMETHYL BENZYLIDENE CAMPHOR | | 113783-61-2 |
| TEA-SALICYLATE | triethanolamine salicylate | 2174-16-5 |
| TEREPHTHALYLIDENE DI-CAMPHOR SULFONIC ACID | 3,3'-(1,4-phenylenedimethylene)bis[7,7-dimethyl-2-oxo-bicyclo[2.2.1]heptane-1-methanesulfonic acid] | 90457-82-2 |
| TITANIUM DIOXIDE | titanium dioxide | 13463-67-7 |
| DIGALLOYL TRIOLEATE | digalloyl trioleate | 17048-39-4 |
| ZINC OXIDE | zinc oxide | 1314-13-2 |
| Methylene bis-benzotriazolyl tetramethylbutylphenol | 2,2'-methylene-bis[6-(2H-benzotriazol-2-yl)-4-(1,1,3,3-tetramethylbutyl)-phenol] | 103597-45-1 |
| Bis-ethylhexyloxyphenol methoxyphenyltriazine | 2,4-bis{[4-(2-ethylhexyloxy)-2-hydroxy]-phenyl}-6-(4-methoxyphenyl)-(1,3,5)-triazine | 187393-00-6 |
| BISIMIDAZYLATE | 1H-benzimidazole-4,6-disulfonic acid, 2,2'-(1,4-phenylene)bis-, disodium salt | 180898-37-7 |
| DIETHYLHEXYL BUTAMIDO TRIAZONE | benzoic acid, 4,4'-[[6-[[4-[[(1,1-dimethylethyl)amino]carbonyl]phenyl]amino]-1,3,5-triazine-2,4-diyl]diimino]bis-, bis(2-ethylhexyl) ester | 154702-15-5 |
| DROMETRIZOLE TRISILOXANE | phenol, 2-(2H-benzotriazol-2-yl)-4-methyl-6-[2-methyl-3-[1,3,3,3-tetramethyl-1-[(trimethylsilyl)oxy]disiloxanyl]propyl]- | 155633-54-8 |
| BENZYLIDENE MALONATE POLYSILOXANE | alpha-(trimethylsilyl)-omega-(trimethyl-silyloxy)poly[oxy(dimethyl)silylene]-co-[oxy(methyl)(2-{p-[2,2-bis(ethoxycarbonyl)vinyl]-phenoxy}-1-methyleneethyl)silylene]-co-[oxy(methyl)(2-{p-[2,2-bis(ethoxycarbonyl)-vinyl]phenoxy}prop-1-enyl)silylene] | 207574-74-1 |
| | 2-(4-diethylamino-2-hydroxybenzoyl)-benzoic hexyl ester | 302776-68-7 |

Each of the above-mentioned light-protective agents, especially the light-protective agents in the above Table indicated as being preferred, can be used in admixture with the silane and siloxane bis(biphenyl)triazine derivatives according to the invention. It will be understood in that connection that, in addition to the mixtures of the bis(biphenyl)triazine derivatives of the present invention, it is also possible for more than one of the additional light-protective agents to be used, for example, two, three, four, five or six further light-protective agents.

Other typical ingredients in such formulations are preservatives, bactericides and bacteriostatic agents, perfumes, dyes, pigments, thickening agents, moisturizing agents, humectants, fats, oils, waxes or other typical ingredients of cosmetic and personal care formulations such as alcohols, poly-alcohols, polymers, electrolytes, organic solvents, silicon derivatives, emollients, emulsifiers or emulsifying surfactants, surfactants, dispersing agents, antioxidants, anti-irritants and anti-inflammatory agents etc.

The cosmetic compositions contain, for example, from 0.1 to 30% by weight, preferably from 0.1 to 15% by weight and especially from 0.5 to 10% by weight, based on the total weight of the composition, of silane and siloxane bis(biphenyl)triazine derivatives of formula (1) and at least one cosmetically tolerable adjuvant.

The cosmetic compositions can be prepared by physically mixing silane and siloxane bis(biphenyl)triazine derivatives of formula (1) with the adjuvant using customary methods, for example by simply stirring together the individual components, especially by making use of the dissolution properties of already known cosmetic UV absorbers, for example OMC, salicylic acid isooctyl ester, inter alia. The UV absorber can be used, for example, without further treatment, or in the micronized state, or in the form of a powder.

The cosmetic compositions may be, for example, creams, gels, lotions, alcoholic and aqueous/alcoholic solutions, emulsions, wax/fat compositions, stick preparations, powders or ointments.

As water- and oil-containing emulsions (e.g. W/O, O/W, O/W/O and W/O/W emulsions or microemulsions) the compositions contain, for example, from 0.1 to 30% by weight, preferably from 0.1 to 15% by weight and especially from 0.5 to 10% by weight, based on the total weight of the composition, of the silane and siloxane bis(biphenyl)triazine derivatives of formula (1), from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically tolerable adjuvants.

As oil components of oil-containing compositions (e.g. oils, W/O, O/W, O/W/O and W/O/W emulsions or microemulsions) there come into consideration, for example, Guerbet alcohols based on fatty alcohols having from 6 to 18, preferably from 8 to 10, carbon atoms, esters of linear $C_6$-$C_{24}$ fatty acids with linear $C_3$-$C_{24}$ alcohols, esters of branched $C_6$-$C_{13}$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, triglycerides based on $C_6$-$C_{10}$ fatty acids, liquid mono/di-/tri-glyceride mixtures based on $C_6$-$C_{18}$ fatty acids, esters of $C_6$-$C_{24}$ fatty alcohols and/or Guerbet alcohols with aromatic carboxylic acids, especially benzoic acid, esters of $C_2$-$C_{12}$-dicarboxylic acids with linear or branched alcohols having from 1 to 22 carbon atoms or polyols having from 2 to 10 carbon atoms and from 2 to 6 hydroxy groups, vegetable oils (such as sunflower oil, olive oil, soybean oil, rapeseed oil, almond oil, jojoba oil, orange oil, wheat germ oil, peach kernel oil and the liquid components of coconut oil), branched primary alcohols, substituted cyclohexanes, linear and branched $C_6$-$C_{22}$ fatty alcohol carbonates, Guerbet carbonates, esters of benzoic acid with linear and/or branched $C_6$-$C_{22}$ alcohols (e.g. Finsolv® TN), linear or branched, symmetric or asymmetric dialkyl ethers having a total of from 12 to 36 carbon atoms, especially from 12 to 24 carbon atoms, for example di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether, n-hexyl n-undecyl ether, di-tert-butyl ether, diisopentyl ether, di-3-ethyldecyl ether, tert-butyl n-octyl ether, isopentyl n-octyl ether and 2-methyl pentyl-n-octyl ether; ring-opening products of epoxidised fatty acid esters with polyols, silicone oils and/or aliphatic or naphthenic hydrocarbons. Also of importance are monoesters of fatty acids with alcohols having from 3 to 24 carbon atoms. That group of substances comprises the esterification products of fatty acids having from 8 to 24 carbon atoms, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols). Of special importance are isopropyl myristate, isononanoic acid $C_{16}$-$C_{18}$ alkyl esters, stearic acid 2-ethylhexyl ester, cetyl oleate, glycerol tricaprylate, coconut fatty alcohol caprinate/caprylate and n-butyl stearate. Further oil components that can be used are dicarboxylic acid esters, such as di-n-butyl adipate, di(2-ethylhexyl) adipate, di(2-ethylhexyl) succinate and diisotridecyl acetate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Preferred mono- or poly-ols are ethanol, isopropanol, propylene glycol, hexylene glycol, glycerol and sorbitol. It is also possible to use di- and/or tri-valent metal salts (alkaline earth metal, $Al^{3+}$ inter alia) of one or more alkyl carboxylic acids.

The oil components can be used in an amount of, for example, from 1 to 60% by weight, especially from 5 to 50% by weight and preferably from 10 to 35% by weight, based on the total weight of the composition.

Any conventionally usable emulsifier can be used for the compositions.

As emulsifiers there come into consideration, for example, non-ionic surfactants from the following groups:
  addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, for example ceteareth-20 or ceteareth-12;
  $C_{12}$-$C_{22}$ fatty acid mono- and di-esters of addition products of from 1 to 30 mol of ethylene oxide with polyols having from 3 to 6 carbon atoms, especially with glycerol;
  glycerol mono- and di-esters and sorbitan mono- and di-esters of saturated and unsaturated fatty acids having from 6 to 22 carbon atoms and ethylene oxide addition products thereof, for example glyceryl stearates, glyceryl isostearates, glyceryl oleates, sorbitan oleates or sorbitan sesquioleates;

$C_8$-$C_{22}$alkyl-mono- and -oligo-glycosides and ethoxylated analogues thereof, degrees of oligomerisation of from 1.1 to 5, especially from 1.2 to 1.4, being preferred, and glucose being preferred as the sugar component;

addition products of from 2 to 60 mol, especially from 15 to 60 mol, of ethylene oxide with castor oil and/or hydrogenated castor oil;

polyol esters and especially polyglycerol esters, for example diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable;

partial esters based on linear, branched, unsaturated or saturated $C_6$-$C_{22}$ fatty acids, ricinoleic acid and also 12-hydroxystearic acid and on glycerol, polyglycerol, pentaerythritol, dipentaerythritol, sugar alcohols (e.g. sorbitol), alkyl glucosides (e.g. methyl glucoside, butyl glucoside, lauryl glucoside) and also polyglucosides (e.g. cellulose), for example polyglyceryl-2-dihydroxystearates or polyglyceryl-2-diricinoleates;

mono-, di- and tri-alkylphosphates and also mono-, di- and/or tri-PEG-alkylphosphates and salts thereof;

wool wax alcohols;

one or more ethoxylated esters of natural derivatives, for example polyethoxylated esters of hydrogenated castor oil;

silicone oil emulsifiers, for example silicone polyol;

polysiloxane/polyalkyl/polyether copolymers and corresponding derivatives, for example cetyl dimethicone copolyol;

mixed esters of pentaerythritol, fatty acids, citric acid and fatty alcohol (see DE-A-1 165 574) and/or mixed esters of fatty acids having from 6 to 22 carbon atoms, methylglucose and polyols, preferably glycerol or polyglycerol, for example polyglyceryl-3-glucose distearates, polyglyceryl-3-glucose dioleates, methyl glucose dioleates or dicocoyl pentaerythryl distearyl citrates and also polyalkylene glycols.

The addition products of ethylene oxide and/or of propylene oxide with fatty alcohols, fatty acids, alkylphenols, glycerol mono- and di-esters and also sorbitan mono- and di-esters of fatty acids, or with castor oil, are known, commercially available products. They are usually homologue mixtures, the average degree of alkoxylation of which corresponds to the ratio of the amounts of ethylene oxide and/or propylene oxide and substrate with which the addition reaction is carried out. $C_{12}$-$C_{18}$ fatty acid mono- and di-esters of addition products of ethylene oxide with glycerol are known, for example, from DE-A-2 024 051 as fat-restoring substances for cosmetic preparations.

$C_8$-$C_{18}$alkyl-mono- and -oligo-glycosides, their preparation and their use are known from the prior art. They are prepared especially by reacting glucose or oligosaccharides with primary alcohols having from 8 to 18 carbon atoms. Suitable glycoside radicals include monoglycolsides in which a cyclic sugar radical is glycosidically bonded to the fatty alcohol and also oligomeric glycosides having a degree of oligomerisation of up to preferably about 8. The degree of oligomerisation is a statistical average value based on a homologue distribution customary for such technical-grade products.

It is also possible to use zwitterionic surfactants as emulsifiers. The term "zwitterionic surfactants" denotes especially surface-active compounds that carry at least one quaternary ammonium group and at least one carboxylate and/or sulfonate group in the molecule. Zwitterionic surfactants that are especially suitable are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate. Special preference is given to the fatty acid amide derivative known by the CTFA name cocamidopropyl betaine. Likewise suitable as emulsifiers are ampholytic surfactants. Ampholytic surfactants are to be understood as meaning especially those which, in addition to containing a $C_8$-$C_{18}$-alkyl or -acyl group, contain at least one free amino group and at least one —COON or —$SO_3H$ group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group.

Ampholytic surfactants to which special preference is given are N-cocoalkylamino-propionate, cocoacylaminoethylaminopropionate and $C_{12}$-$C_{18}$acylsarcosine. In addition to the ampholytic emulsifiers there also come into consideration quaternary emulsifiers, special preference being given to those of the esterquat type, preferably methyl-quaternised di-fatty acid triethanolamine ester salts.

Non-ionic emulsifiers are preferred. Of the non-ionic emulsifiers mentioned, special preference is given to ethoxylated fatty alcohols having from 8 to 22 carbon atoms and from 4 to 30 EO units.

The emulsifiers may be used in an amount of, for example, from 1 to 30% by weight, especially from 4 to 20% by weight and preferably from 5 to 10% by weight, based on the total weight of the composition. It is, however, also possible in principle to dispense with the use of emulsifiers.

The compositions according to the invention, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, pearlescent waxes, consistency regulators, thickeners, polymers, silicone compounds, fats, waxes, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilizers, perfume oils, colorants, bacteria-inhibiting agents and the like.

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Examples of suitable mild surfactants, that is to say surfactants especially well tolerated by the skin, include fatty alcohol polyglycol ether sulfates, monoglyceride sulfates, monoand/or di-alkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensation products, the latter preferably being based on wheat proteins.

As pearlescent waxes there come into consideration, for example: alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

As consistency regulators there come into consideration especially fatty alcohols or hydroxy fatty alcohols having from 12 to 22 carbon atoms and preferably from 16 to 18 carbon atoms, and in addition partial glycerides, fatty acids and hydroxy fatty acids. Preference is given to a combination of such substances with alkyl-oligoglucosides and/or fatty acid N-methylglucamides of identical chain length and/or polyglycerol poly-12-hydroxystearates. Suitable thickeners include, for example, Aerosil types (hydrophilic silicic acids), polysaccharides, especially xanthan gum, guar-guar, agar-agar, alginates and Tyloses, carboxymethyl cellulose and hydroxymethyl cellulose, also relatively high molecular weight polyethylene glycol mono- and di-esters of fatty acids, polyacrylates (e.g. Carbopol® from Goodrich or Synthalen® from Sigma), polyacrylamides, polyvinyl alcohol and polyvinylpyrrolidone, surfactants, for example ethoxylated fatty acid glycerides, esters of fatty acids with polyols, for example pentaerythritol or trimethylolpropane, fatty alcohol ethoxylates with restricted homologue distribution and alkyl-oligoglucosides as well as electrolytes, such as sodium chloride or ammonium chloride.

Suitable cationic polymers are, for example, cationic cellulose derivatives, for example a quaternised hydroxymethyl cellulose obtainable under the name Polymer JR 400® from Amerchol, cationic starch, copolymers of diallylammonium salts and acrylamides, quaternised vinylpyrrolidone/vinyl imidazole polymers, for example Luviquat® (BASF), condensation products of polyglycols and amines, quaternised collagen polypeptides, for example lauryldimonium hydroxypropyl hydrolyzed collagen (Lamequat®L/Grünau), quaternised wheat polypeptides, polyethyleneimine, cationic silicone polymers, for example amidomethicones, copolymers of adipic acid and dimethylaminohydroxypropyldiethylenetriamine (Cartaretin®/Sandoz), copolymers of acrylic acid with dimethyldiallylammonium chloride (Merquat® 550/Chemviron), polyaminopolyamides, as described, for example, in FR-A-2 252 840, and the crosslinked water-soluble polymers thereof, cationic chitin derivatives, for example quaternised chitosan, optionally distributed as microcrystals; condensation products of dihaloalkyls, for example dibromobutane, with bisdialkylamines, for example bisdimethylamino-1,3-propane, cationic guar gum, for example Jaguar® C-17, Jaguar® C-16 from Celanese, quaternised ammonium salt polymers, for example Mirapol® A-15, Mirapol® AD-1, Mirapol® AZ-1 from Miranol.

As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octyl acrylamide/methyl methacrylate/tert-butylaminoethyl methacrylate/2-hydroxypropyl methacrylate copolymers, polyvinylpyrrolidone, vinyl pyrrolidone/vinyl acetate copolymers, vinylpyrrolidone/dimethylaminoethyl methacrylate/vinyl caprolactam terpolymers and also optionally derivatised cellulose ethers and silicones.

Suitable silicone compounds are, for example, dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Also suitable are simethicones, which are mixtures of dimethicones having an average chain length of from 200 to 300 dimethylsiloxane units with hydrogenated silicates. A detailed survey by Todd et al., of suitable volatile silicones may in addition be found in Cosm. Toil. 91, 27 (1976).

Typical examples of fats are glycerides, and as waxes there come into consideration, inter alia, beeswax, carnauba wax, candelilla wax, montan wax, paraffin wax, hydrogenated castor oils and fatty acid esters or microwaxes solid at room temperature optionally in combination with hydrophilic waxes, e.g. cetylstearyl alcohol or partial glycerides. Metal salts of fatty acids, for example magnesium, aluminium and/or zinc stearate or ricinoleate, may be used as stabilisers.

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

As deodorising active ingredients there come into consideration, for example, antiperspirants, for example aluminium chlorohydrates (see J. Soc. Cosm. Chem. 24, 281 (1973)). Under the trade mark Locron® of Hoechst AG, Frankfurt (FRG), there is available commercially, for example, an aluminium chlorohydrate corresponding to formula $Al_2(OH)_5Cl \times 2.5H_2O$, the use of which is especially preferred (see J. Pharm. Pharmacol. 26, 531 (1975)). Besides the chlorohydrates, it is also possible to use aluminium hydroxy-acetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen® CAT, Henkel KGaA, Düsseldorf/FRG), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the microbial flora and kill, or inhibit the growth of, sweat-decomposing bacteria can likewise be present in the preparations (especially in stick preparations). Examples include chitosan, phenoxyethanol and chlorhexidine gluconate. 5-Chloro-2-(2,4-dichlorophenoxy)-phenol (Irgasan®, Ciba Specialty Chemicals Inc.) has also proved especially effective.

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds. As swelling agents for aqueous phases there may be used montmorillonites, clay mineral substances, Pemulen and also alkyl-modified types of Carbopol (Goodrich). Further suitable polymers and swelling agents can be found in the review by R. Lochhead in Cosm. Toil. 108, 95 (1993).

In addition to the primary light-protective substances it is also possible to use secondary light-protective substances of the antioxidant kind which interrupt the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, γ-linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine) in very small tolerable amounts (e.g. from pmol to μmol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, α-glycosylrutin, ferulic acid, furfurylidene glucitol, carnosine, butyl hydroxytoluene, butyl hydroxyanisole, resinous nordihydroguaiaretic acid, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl] sulfanilic acid (and salts thereof, for example the sodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned. The amount of antioxidants present is usually from 0.001 to 30% by weight, preferably from 0.01 to 3% by weight, based on the weight of the UV absorber(s).

To improve the flow behavior it is also possible to employ hydrotropic agents, for example ethanol, isopropyl alcohol or polyols. The polyols that come into consideration for that purpose have preferably from 2 to 15 carbon atoms and at least two hydroxy groups.

The polyols may also contain further functional groups, especially amino groups, and/or may be modified with nitrogen. Typical examples are as follows:
glycerol;
alkylene glycols, for example ethylene glycol, diethylene glycol, propylene glycol, butylene glycol, hexylene glycol and also polyethylene glycols having an average molecular weight of from 100 to 1000 dalton;
technical oligoglycerol mixtures having an intrinsic degree of condensation of from 1.5 to 10, for example technical diglycerol mixtures having a diglycerol content of from 40 to 50% by weight;
methylol compounds, such as, especially, trimethylolethane, trimethylolpropane, trimethyl-olbutane, pentaerythritol and dipentaerythritol;
lower alkyl-glucosides, especially those having from 1 to 8 carbon atoms in the alkyl radical, for example methyl and butyl glucoside;
sugar alcohols having from 5 to 12 carbon atoms, for example sorbitol or mannitol;
sugars having from 5 to 12 carbon atoms, for example glucose or saccharose;
amino sugars, for example glucamine;
dialcohol amines, such as diethanolamine or 2-amino-1,3-propanediol.

Suitable preservatives include, for example, phenoxyethanol, formaldehyde solution, Parabens, pentanediol or sorbic acid and the further substance classes listed in Schedule 6, Parts A and B of the Cosmetics Regulations.

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type.

Aromatic substance compounds of the ester type are, for example, benzyl acetate, phenoxy-ethyl isobutyrate, p-tert-butylcyclohexyl acetate, linalyl acetate, dimethyl-benzyl-carbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, α-isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, α-hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, β-damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

There may be used as colourants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colourants are usually used in concentrations of from 0.001 to 0.1% by weight, based on the total mixture.

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide).

A large number of aromatic substances and ethereal oils also have antimicrobial properties. Typical examples are the active ingredients eugenol, menthol and thymol in clove oil, mint oil and thyme oil. A natural deodorizing agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

It is furthermore possible for the cosmetic compositions to contain, as adjuvants, antifoams, such as silicones, structurants, such as maleic acid, solubilizers, such as ethylene glycol, propylene glycol, glycerol or diethylene glycol, opacifiers, such as latex, styrene/PVP or styrene/acrylamide copolymers, complexing agents, such as EDTA, NTA, β-alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or α-mercaptoethanesulfonic acid, or oxidizing agents, such as hydrogen peroxide, potassium bromate or sodium bromate.

There come into consideration as insect repellents, for example, N,N-diethyl-m-toluamide, 1,2-pentanediol or insect repellent 3535; suitable self-tanning agents are, for example, dihydroxyacetone, erythrulose or mixtures of dihydroxyacetone and erythrulose.

Cosmetic formulations according to the invention are contained in a wide variety of cosmetic preparations. There come into consideration, for example, especially the following preparations:

skin-care preparations, e.g. skin-washing and cleansing preparations in the form of tablet-form or liquid soaps, synthetic detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshade preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidising dyes, or natural hair colorants, such as henna or camomile.

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellant gas or pump-action spray) or an aerosol, in the form of a foam, or in the form of a paste.

Of special importance as cosmetic compositions for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection oils, sun protection milk and sun protection preparations in the form of a spray.

Of special importance as cosmetic compositions for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:

$a_1$) spontaneously emulsifying stock formulation, consisting of the UV absorber according to the invention, PEG-6-$C_{10}$oxoalcohol and sorbitan sesquioleate, to which water and any desired quaternary ammonium compound, for example 4% minkamidopropyldimethyl-2-hydroxyethylammonium chloride or Quaternium 80 is added;

$a_2$) spontaneously emulsifying stock formulation consisting of the UV absorber according to the invention, tributyl citrate and PEG-20-sorbitan monooleate, to which water and any desired quaternary ammonium compound, for example 4% minkamidopropyldimethyl-2-hydroxyethylammonium chloride or Quaternium 80 is added;

b) Quat-doped solutions of the UV absorber according to the invention in butyltriglycol and tributyl citrate;

c) mixtures or solutions of the UV absorber according to the invention with n-alkylpyrrolidone.

The following examples illustrate the present invention without limiting.

EXAMPLE 1

Synthesis of Siloxane Bisbiphenyl Triazine S-1

0.72 g (0.00315 mol, 97%) of 1,1,1,3,5,5,5-heptamethyltrisiloxane were added to a mixture of 1.60 g (0.003 mol) of the allyl bisbiphenyl triazine 2-[4,6-bis([1,1'-biphenyl]-4-yl)-1,3,5-triazine-2-yl]-5-(2-propene-1-yloxy)-phenol (CAS-No. 357436-15-8; B-19) corresponding to formula

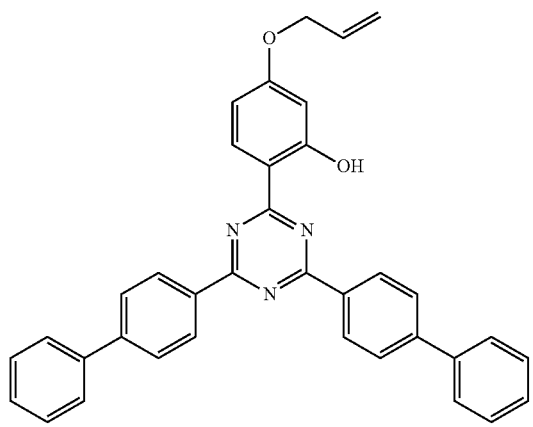

and 15 drops of platinum(0)-1,3-divinyl-1,1,3,3-tetramethyldisiloxane complex (soln. in poly(dimethylsiloxane, vinyl terminated, purchased from the company Aldrich) dissolved in 25 ml of toluene at 65° C. Heating was continued at 120° C. for 18 h. After adding 25 mL of ethanol and 1 g of charcoal the mixture was stirred at 80° C. for 1 h. The solid was filtered off and washed with a little amount of a 1/1 ethanol/toluene mixture. The filtrate was concentrated under vacuo, dried at 70-80° C. resulting in a highly viscous oil which solidifies on standing.

1,709 g (75% yield) of a yellowish powder.

UV(tetrahydrofurane): $\lambda_{max}$=319 nm; $\epsilon$=72200 $M^{-1}$ $cm^{-1}$.

EXAMPLE 2

Synthesis of Silane Bisbiphenyl Triazine S-2

The product was prepared analogously to example 1 by reacting 1.60 g (3 mmol) of the allyl bisbiphenyl triazine B-19, 0.39 g (3.3 mmol) triethyl silane and 15 drops of the platinum(0)-catalyst in 25 ml toluene.

1.55 g (80% yield) of a yellow resin was obtained which solidifies after several hours. On grinding a yellowish powder was obtained.

UV (tetrahydrofurane): $\lambda_{max}$=319 nm, $\epsilon$=76300 $M^{-1}$ $cm^{-1}$.

EXAMPLE 3

Synthesis of Siloxane Bisbiphenyl Triazine S-3

The product was prepared analogously to example 1 by reacting 1.60 g (3 mmol) of the allyl bisbiphenyl triazine B-19, 5.42 g (3.3 mmol) poly(dimethylsiloxane) (mono-hydrogen and mono-n-butyl terminated, average Mw=1000 Dalton, product name Silaplane FM-0111 purchased from Chisso Corp.) and 15 drops of the platinum(0)-catalyst in 25 ml toluene.

4.07 g (~88% yield) of an yellow wax was obtained.

UV(tetrahydrofurane): $\lambda_{max}$=319 nm, $\epsilon$=68200 $M^{-1}$ $cm^{-1}$.

EXAMPLE 4

Synthesis of Siloxane Bisbiphenyl Triazine S-4

The product was prepared analogously to example 1 by reacting 1.60 g (3 mmol) of the allyl bisbiphenyl triazine B-19, 0.82 g (0.5 mmol) poly(dimethylsiloxane-co-methylhydrosilane) (trimethylsilyl terminated, average Mw=1500 Dalton, 33 mol % MeHSiO) and 15 drops of the platinum(0)-catalyst in 25 ml toluene.

1.13 g (~50% yield) of an yellow resin was obtained which solidifies after several hours. On grinding a yellowish powder was obtained.

UV (tetrahydrofurane): $\lambda_{max}$=316 nm, $\epsilon$=35650 $M^{-1}$ $cm^{-1}$.

EXAMPLE 5

Synthesis of Siloxane Bisbiphenyl Triazine S-5

The product was prepared analogously to example 1 by reacting 1.60 g (3 mmol) of the allyl bisbiphenyl triazine B-19, 0.96 g (1.7 mmol) poly(dimethylsiloxane) (hydride terminated, average $M_n$~580, CAS No. 70900-21-9, purchased from Aldrich) and 15 drops of the platinum(0)-catalyst in 25 ml toluene.

1.88 g (76% yield) of an yellow resin was obtained which solidifies after several hours. On grinding a yellowish powder was obtained.

Melting point: 46.8° C. UV (tetrahydrofurane): $\lambda_{max}$=319 nm, $\epsilon$=118100 $M^{-1}$ $cm^{-1}$.

EXAMPLE 6

Synthesis of Siloxane Bisbiphenyl Triazine S-6

The product was prepared analogously to example 1 by reacting 1.15 g (2.2 mmol) of the allyl bisbiphenyl triazine B-19, 0.15 g (0.6 mmol) 2,4,6,8-tetramethylcyclotetrasiloxane and 15 drops of the platinum(0)-catalyst in 25 ml toluene.

0.34 g of an yellow resin was obtained which solidifies after several hours. On grinding a brownish powder was obtained.

Melting point: 115.5° C.
UV (tetrahydrofurane): $\lambda_{max}$=319 nm, $\epsilon$=29300 $M^{-1}$ $cm^{-1}$.

EXAMPLE 7

Synthesis of Siloxane Bisbiphenyl Triazine S-7

The product was prepared analogously to example 1 by reacting 1.15 g (2.2 mmol) of the allyl bisbiphenyl triazine B-19, 0.71 g (0.5 mmol) poly(dimethylsiloxane-co-methylhydrosilane) (trimethylsilyl terminated, Mw=1500 Dalton, 24 mol % MeHSiO) and 15 drops of the platinum(0)-catalyst in 25 ml toluene.

1.44 g of a brownish resin was obtained which solidifies after several hours. Upon grinding a beige powder was obtained.

Melting point: 79.7° C.
UV (tetrahydrofuran): $\lambda_{max}$=318 nm, $\epsilon$=31300 $M^{-1}$ $cm^{-1}$.

EXAMPLE 8

Synthesis of Siloxane Bisbiphenyl Triazine S-8

The product was prepared analogously to example 1 by reacting 1.15 g (2.2 mmol) of the allyl bisbiphenyl triazine B-19, 0.56 g (3.3 mmol) triethoxylsilane and 15 drops of the platinum(0)-catalyst in 25 ml toluene.

0.57 g of a yellowish resin was obtained which solidifies after several hours. Upon grinding a yellowish powder was obtained.

Melting point: 62.23° C.
UV (tetrahydrofuran): $\lambda_{max}$=320 nm, $\epsilon$=75800 $M^{-1}$ $cm^{-1}$.
Solubility

| Measurement of Solubility | |
|---|---|
| Comp. No. | Solubility in Capric/Caprylic Triglyceride [w-%] |
| (S-1) | 11.7 |
| (S-2) | 22.8 |
| (S-3) | 26.4 |
| (S-5) | 21.7 |

The solubility data of the bisbiphenyl triazine derivatives S-1, S-2, S-3 and S-5 containing silane and/or siloxane groups according to the instant invention suggest that the novel bisbiphenyl triazine derivatives are particularly highly oilsoluble UV absorbers.

Photostability
Measurement of Photostability

The method used for assessment of photostability is based on the irradiation of a highly diluted solution of the UV-filter. The analysis after certain doses of irradiation was performed by UV-spectroscopy. The concentration of the UV-absorber in ethanol is adjusted to values between $1 \cdot 10^5$ and $1 \cdot 10^5$ mol/l, such that the absorbance of the solution in cuvette of 1 cm optical pathlength is equal or smaller than 0.2. The mutual protection of filter molecules can be excluded under such conditions.

Prior to irradiation of a sample the UVB-intensity at the sample position is measured with a UV-radiometer (RM-12, Dr. Grobel Electronic GmbH). This radiometer was calibrated by comparison with a measurement of the spectral output of the metal halide lamp (including light guide and cut-off filter) using a wavelength-resolved radiometer (Gamma C11). Therefore the relationship of the reading of the RM-12 radiometer and the corresponding spectral output of the lamp is known, and one is able to determine the wavelength-resolved intensities by measuring the UVB-intensity. By changing the distance between the end of the light guide and the cuvette, the UVB-intensity can be varied in the range of 100 $\mu W/cm^2$ and 4500 $\mu W/cm^2$.

For sample irradiation the highest possible intensity was used (4.5 $mW/cm^2$ UVB-intensity measured with the Macam 103 radiometer). The irradiation time was varied from 0 to 180 min. The dose the sample has received after 180 minutes corresponds to 60 MED. During irradiation the sample was stirred. After certain intervals of irradiation, the samples were analysed in a UV-spectrometer (Perkin Elmer, Lambda 16).

From the absorbance values at each dose of irradiation the concentration may be calculated using Lambert-Beer's law. In order to get the half-life of the substance, a first order kinetic model was fitted to the experimental data. Since the UV-spectrum of the lamp and the UV-spectrum of the COLIPA standard sun are known, one can calculate the respective half-life of the UV-absorber under conditions of COLIPA standard sun irradiation [Bernd Herzog, Stefan Müller, Myriam Sohn, Uli Osterwalder, "New Insight and Prediction of Photostablity of Sunscreens", SÖFW Journal 133, 26-36 (2007)].

The investigated half-time values and recovery after irradiation (10 MED) of some specific benzotropolones are listed in the table below:

| Comp. No. | Half time [h] | Recovery after 10MED [%] |
|---|---|---|
| (S-1) | 444.4 | 99.6 |
| (S-2) | 412.1 | 99.6 |
| (S-3) | 282.0 | 99.4 |
| (S-4) | 390.7 | 99.6 |
| (S-5) | 326.2 | 99.5 |
| (S-6) | 363.7 | 99.5 |
| (S-7) | 207.7 | 99.2 |
| (S-8) | 342.2 | 99.5 |

The compounds Nos. S-1, S-2, S-3, S-4, S-5, S-6, S-7 and S-8 according to the present invention possess high photostability and in all cases more than 99% of the silanes and siloxanes are recovered after irradiation of 10 MED.

UV Shielding Properties

The UV shielding properties of the bisbiphenyl triazine derivatives were investigated by measuring their UV spectra in ethanol. In the following table the investigated absorption maxima ($\lambda_{max}$) together with the corresponding $A^{1\%}_{1cm}$ values are listed.

| Comp. No. | Absorption maximum | |
|---|---|---|
| | $\lambda_{max}$ | $A^{1\%}_{1\,cm}$ |
| (S-1) | 319 | 955 |
| (S-2) | 319 | 1175 |
| (S-3) | 319 | 443 |
| (S-4) | 316 | 760 |
| (S-5) | 319 | 717 |
| (S-6) | 319 | 1234 |
| (S-7) | 318 | 751 |
| (S-8) | 320 | 1086 |

The bis(biphenyl)triazine compounds Nos. S-1, S-2, S-3, S-4, S-5, S-6, S-7 and S-8 according to the present invention possess high shielding properties in the UV region as indicated by $A^{1\%}_{1\,cm}$ values above 700.

The invention claimed is:

1. A method of providing a sunscreen composition by adding to a cosmetic composition silane or siloxane bis(biphenyl)triazine UV absorber derivatives of formula

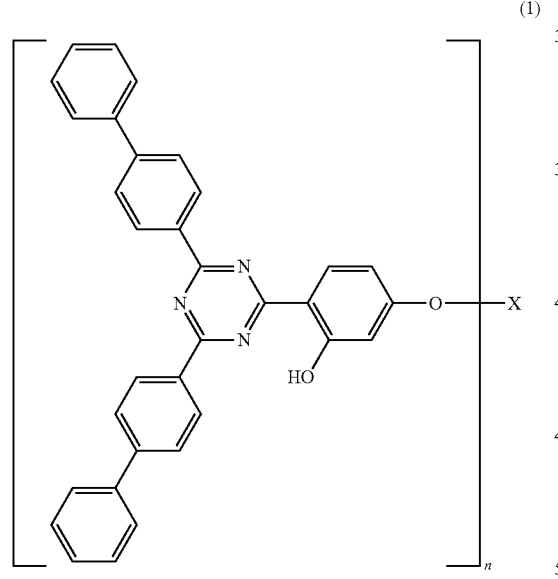

(1)

wherein n is a number from 1 to 4;

if n=1,

X is *-L-Sil; or a radical of formula

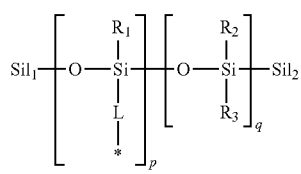

L is a linker selected from a radical of formula (2)

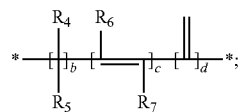

$R_1$, $R_2$, $R_3$ independently from each other are $C_1$-$C_{22}$alkyl; $C_6$-$C_{20}$aryl; $C_1$-$C_{22}$alkoxy; or O—$C_6$-$C_{20}$aryl;

$R_4$, $R_5$, $R_6$ and $R_7$ independently from each other are hydrogen; $C_1$-$C_{22}$alkyl; $C_6$-$C_{20}$aryl; $C_1$-$C_{22}$alkoxy; or O—$C_6$-$C_{20}$aryl;

b is a number from 0 to 30;

c is a number from 0 to 6; and d is a number from 0 to 1;

p is a number from 1 to 250;

q is a number from 0 to 250; and

Sil, $Sil_1$ and $Sil_2$ independently from each other are a silane-, oligosiloxane or polysiloxane moiety;

if n=2,

X is a bivalent radical of formula (1a)

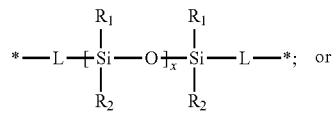

(1b)

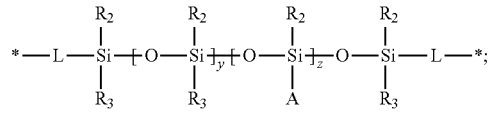

x is a number from 2 to 250;

y is a number from 0 to 250; and z is a number from 1 to 50;

if n=3,

X is a trivalent radical containing a silane-, oligosiloxane or polysiloxane moiety;

If n=4,

X is a tetravalent radical of formula (1c)

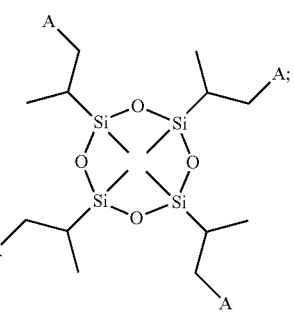

and
A is a radical of formula

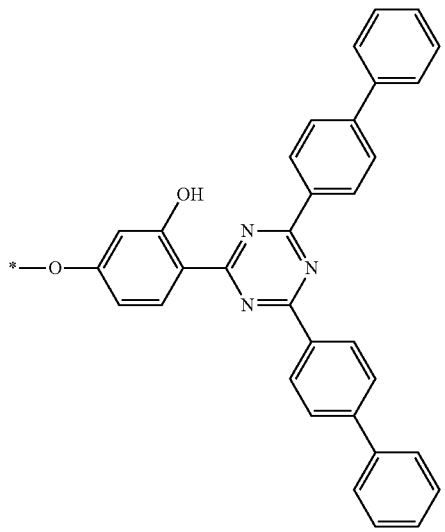

2. The method according to claim 1, wherein in formula (1)
n is a number from 1 to 4;
if n=1,
X is *-L-Sil;
L is a linker selected from a radical of formula (2)

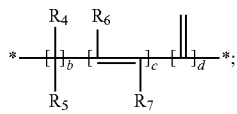

$R_4$, $R_5$, $R_6$ and $R_7$ independently from each other are hydrogen; $C_1$-$C_{22}$alkyl; $C_6$-$C_{20}$aryl; $C_1$-$C_{22}$alkoxy; or O—$C_6$-$C_{20}$aryl;
b is a number from 0 to 30;
c is a number from 0 to 6; and
d is a number from 0 to 1;
Sil, $Sil_1$ and $Sil_2$ independently from each other are a silane-, oligosiloxane or polysiloxane moiety;
if n=2,
X is a bivalent radical of formula (1a)

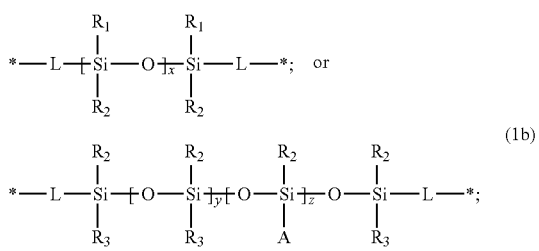

$R_1$, $R_2$, $R_3$ independently from each other are $C_1$-$C_{22}$alkyl; $C_6$-$C_{20}$aryl; $C_1$-$C_{22}$alkoxy; or O—$C_6$-$C_{20}$aryl;
x is a number from 2 to 250;
y is a number from 0 to 250; and
z is a number from 1 to 50;
if n=3, X is a trivalent radical containing a silane-, oligosiloxane or polysiloxane moiety;
If n=4,
X is a tetravalent radical of formula

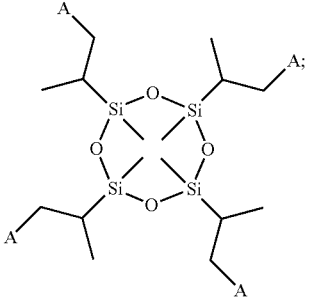

and
A is a radical of formula

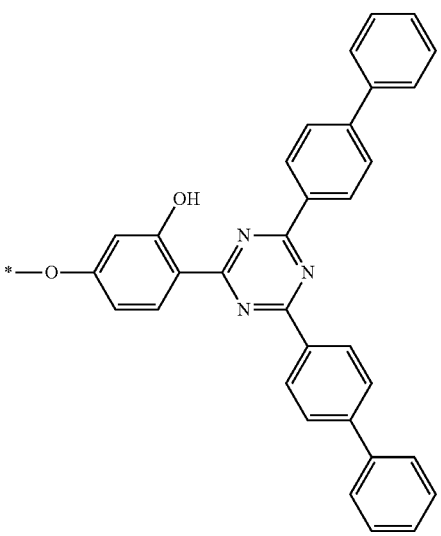

3. The method according to claim 1, wherein
Sil, $Sil_1$ and $Sil_2$ independently from each other are an oligosiloxane moiety selected from
$Si(R_1)_m[OSi(R_2)]_o$; wherein
m is 0; 1; or 2,
o is 3, 2 or 1;
the sum of m and o are 3; and
$R_1$ and $R_2$ independently from each other are $C_1$-$C_{22}$alkyl; $C_6$-$C_{20}$aryl; $C_1$-$C_{22}$alkoxy; or O—$C_6$-$C_{20}$aryl.
4. The method according to claim 1, wherein the silane groups are selected from trimethylsilane, triethylsilane, tripropylsilane, triisopropylsilane, dimethyl tert-butylsilane, dimethylhexylsilane, triphenylsilane and dimethylphenylsilane.
5. The method according to claim 1, wherein in formula (2)
$R_4$ and $R_5$, independently from each other are hydrogen; or $C_1$-$C_{22}$alkyl;
b is a number from 1 to 30; and
c and d are 0.
6. The method according claim 5, wherein in formula (2)
$R_4$ and $R_5$, independently from each other are hydrogen; or $C_1$-$C_5$alkyl.

7. The method according to claim 5, wherein in formula (2) $R_4$ and $R_5$, independently from each other are hydrogen; or methyl.

8. The method according to claim 5, wherein in formula (2) b is a number from 1 to 5.

9. The method according to claim 1, wherein X corresponds to the formula

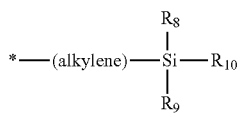
(3)

wherein

"alkylene" denotes a straight chained or branched $C_2$-$C_{12}$alkylene;

$R_8$, $R_9$ and $R_{10}$ independently from each other are $C_1$-$C_{22}$alkyl; or $C_1$-$C_{22}$alkoxy; or a radical of formula

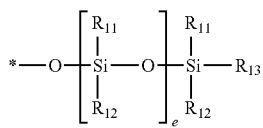
(3a)

$R_{11}$ and $R_{12}$ and $R_{13}$ independently from each other are $C_1$-$C_{22}$alkyl; or $C_1$-$C_{22}$alkoxy; and e is a number from 0 to 30.

10. The method according to claim 1, wherein X is a radical of formula

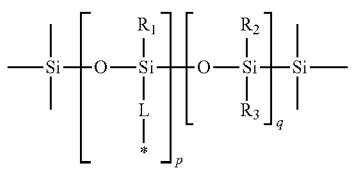

wherein p and q independently from each other are a number from 1 to 20.

11. The method according to claim 10, wherein p and q independently from each other are a number from 3 to 15.

12. Compounds of formula

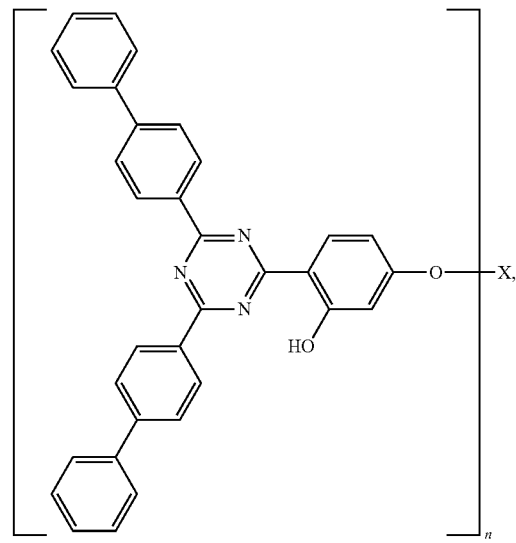
(1)

wherein
n is a number from 1 to 4;
if n=1,
X is *-L-Sil; or a radical of formula

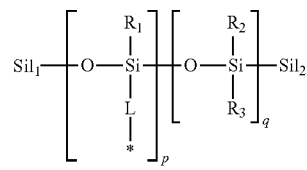

L is a linker selected from a radical of formula (2)

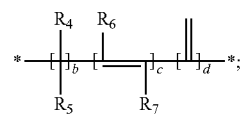

$R_4$, $R_5$, $R_6$ and $R_7$ independently from each other are hydrogen; $C_1$-$C_{22}$alkyl; $C_6$-$C_{20}$aryl; $C_1$-$C_{22}$alkoxy; or O—$C_6$-$C_{20}$aryl;
b is a number from 0 to 30;
c is a number from 0 to 6; and
d is a number from 0 to 1;
p is a number from 1 to 250;
q is a number from 0 to 250; and
Sil, $Sil_1$ and $Sil_2$ independently from each other are a silane-, oligosiloxane or polysiloxane moiety;
if n=2,
X is a bivalent radical of formula (1a)

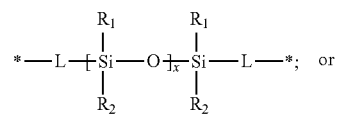 or

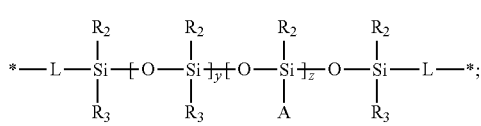

(1b)

R₁, R₂, R₃ independently from each other are $C_1$-$C_{22}$alkyl; $C_6$-$C_{20}$aryl; $C_1$-$C_{22}$alkoxy; or O—$C_6$-$C_{20}$aryl;
x is a number from 2 to 250;
y is a number from 0 to 250; and
z is a number from 1 to 50;
if n=3,
X is a trivalent radical containing a silane-, oligosiloxane or polysiloxane moiety;
If n=4,
X is a tetravalent radical of formula

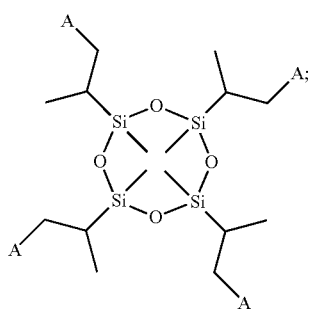

(1c)

and

A is a radical of formula

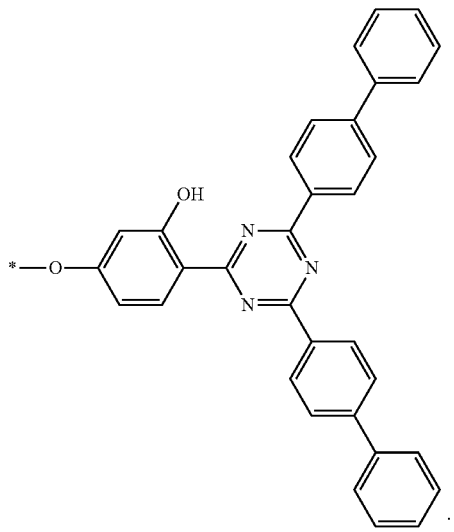

13. Cosmetic composition comprising a triazine derivative of formula (1) according to claim 1, and at least one cosmetic acceptable carrier.

* * * * *